United States Patent [19]

Wickett et al.

[11] 4,163,800
[45] Aug. 7, 1979

[54] TOPICAL COMPOSITION AND TREATMENT OF SKIN LESIONS THEREWITH

[75] Inventors: Richard R. Wickett, Hamilton; William R. Kock, Cincinnati, both of Ohio

[73] Assignee: The Procter & Gamble Company, Cincinnati, Ohio

[21] Appl. No.: 825,363

[22] Filed: Aug. 17, 1977

[51] Int. Cl.² ................. A61K 31/085; A61K 31/155
[52] U.S. Cl. ..................................... 424/326; 424/62; 424/130; 424/338; 424/DIG. 13
[58] Field of Search ................. 424/62, 130, 326, 338, 424/DIG. 13

[56] References Cited

U.S. PATENT DOCUMENTS

| | | | |
|---|---|---|---|
| 1,576,774 | 3/1926 | McGraw | 424/62 |
| 2,620,301 | 12/1952 | McLeod | 252/33.4 X |
| 2,877,269 | 3/1959 | Van Campen, Jr. | 424/326 X |
| 3,312,589 | 4/1967 | Entley | 424/326 X |
| 3,512,181 | 10/1964 | Shapiro | 424/326 X |
| 3,535,422 | 10/1970 | Cox | 424/338 |
| 3,628,941 | 12/1971 | Marks | 424/358 X |
| 3,769,427 | 10/1973 | Hughes | 424/326 |
| 4,046,919 | 9/1977 | Cebrian | 424/338 |

FOREIGN PATENT DOCUMENTS

| | | | |
|---|---|---|---|
| 2263130 | 6/1973 | Fed. Rep. of Germany . | |
| 2417872 | 10/1974 | Fed. Rep. of Germany | 424/326 |
| 1218107 | 12/1959 | France | 424/326 |
| 809165 | 2/1959 | United Kingdom | 426/326 |
| 1163044 | 9/1969 | United Kingdom . | |
| 1185685 | 3/1970 | United Kingdom | 424/338 |
| 1407937 | 10/1975 | United Kingdom . | |

OTHER PUBLICATIONS

Hegna, J. Pharm. Pharmac., vol. 28, 1976, pp. 261–262.
The Condensed Chem. Dict., Van Nostrand-Reinhold Co., 7th Ed., p. 461.
The Extra Pharm., Martindale, 26th Ed., p. 2017.
Kirton, Br. J. Clin. Prac., vol. 21, 1967, pp. 127–128.
Liddell, Br. J. Clin. Prac., vol. 28, 1974, pp. 379–382.
Kuflik, Cutis, vol. 17, 1976, pp. 175–177.
Wilkinson, Can. Med. Asso. J., vol. 95, 1966, pp. 28–29.
Fulton, Arch. Derm., vol. 110, 1974, pp. 83–86.
Hare, Br. J. Clin. Prac., vol. 29, 1973, pp. 63–66.
Mysliborski, AFP, vol. 15, 1977, pp. 86–91.
Vasarinsh, Arch Derm., vol. 98, 1968, pp. 183–187.
Pace, Can. Med. Asso. J., vol. 93, 1965, pp. 282–284.
Eaglstein, Arch Derm., vol. 97, 1968, p. 527.
Poole, Arch Derm., vol. 102, 1970, pp. 400–404.
Brogden, Drugs, vol. 8, 1974, pp. 417–421.
Levine, Ohio State Med. J., vol. 65, 1969, pp. 492–494.
Purmal, Chem. Abs., vol. 58, 1963, p. 3937.
Ellis, Progress in Med. Chem., Butterworths, Wash., DC, vol. 3, 1963, p. 7.
Harry's Cosmeticology, The Principles & Practice of Mod. Cos., Leonard Hill Books, London, 6th Ed., vol. I, 1973, pp. 556–561, 647.

Primary Examiner—Anna P. Fagelson
Attorney, Agent, or Firm—Walter L. Stumpf; Jerry J. Yetter; Richard C. Witte

[57] ABSTRACT

Compositions and process employing guanidine compounds and peroxide compounds for treatment of acne and other skin lesions by topical application.

2 Claims, No Drawings

TOPICAL COMPOSITION AND TREATMENT OF SKIN LESIONS THEREWITH

BACKGROUND OF THE INVENTION

This invention relates to topical compositions comprising guanidine compounds and peroxide compounds and processes for the conjoint use of such compounds. More particularly, the invention relates to topical compositions for the treatment of skin lesions and methods for treating skin lesions whereby the irritation commonly produced by peroxide compounds is reduced.

Acne and seborrhea are conditions of the human skin characterized by an excessive flow of sebum, or skin oil, from the sebaceous glands located in the pilosebaceous apparatus. Sebum reaches the skin surface through the duct of the hair follicle. The presence of excessive amounts of sebum in the duct and on the skin acts to block or stagnate the continuous flow of sebum from the follicular duct, thus producing a thickening and a solidification of the sebum to form a solid plug known as a comedone. When this process occurs, hyperkeratinization of the follicular opening is stimulated, thus completely closing the duct. The usual results are papules, pustules, or cysts, often contaminated with bacteria which cause secondary infections. Acne is particularly characterized by the presence of comedones, inflammatory papules, pustules, or cysts. The effect of acne ranges from slight skin irritation and pitting to disfiguring scars.

Many topical therapeutic agents are employed in the treatment of acne and seborrhea to prevent the blocking of the follicular duct, to reopen the duct once it has become blocked, to act against the infecting bacteria or the thickened sebum, and to provide combinations of each of these actions. The horny outer layer of the skin (stratum corneum) is formed of dead cells composed largely of keratin. Therapeutic agents which act to prevent the blocking of the follicular duct by promoting the removal of sluffing off of excess keratin are known as keratolytic agents. Sulfur, resorcinol and salicylic acid have been used as keratolytic agents in the treatment of acne.

For over sixty years, benzoyl peroxide has been used as a keratolytic agent in the topical treatment of skin lesions such as burns, varicose ulcers, sycosis vulgaris, seborrhea, and acne. Benzoyl peroxide, $(C_6H_5CO)_2O_2$, is a colorless, odorless, tasteless, crystalline solid, stable at ordinary room temperatures; it is a powerful oxidizing agent, yet nontoxic to man. As noted, benzoyl peroxide has been used as a very effective keratolytic and antibacterial agent in the treatment of acne. While benzoyl peroxide is an effective topical agent for the treatment of skin lesions such as appear in acne or seborrhea, it has the undesirable side effect of being a contact irritant. Accordingly, some patients are denied the benefits of peroxide acne therapy because of the irritation problem.

It has now been discovered that guanidine compounds used in conjunction with a peroxide compound will reduce the skin irritation caused by the peroxide compound.

RELATED REFERENCES

When used in the treatment of acne, benzoyl peroxide produces dryness, exfoliation, and a decrease in bacterial flora. The use of benzoyl peroxide in topical compositions for treating skin lesions such as burns, varicose ulcers, sycosis vulgaris, and acne has been known for some 60 years. Levine, et al., Ohio State Med. J. 65, 492 (1969).

Benzoyl peroxide formulations for the treatment of acne are disclosed in the following references: U.S. Pat. No. 3,535,422, Cox, et al., Oct. 20, 1970; British Pat. Nos. 1,185,685, Fisher, Mar. 25, 1970; 1,163,044 Stiefel Laboratories, Inc., Sept. 4, 1969; and 1,407,937 Stiefel Laboratories, Inc., Oct. 1, 1975.

The use of benzoyl peroxide and benzoyl peroxide compositions for the treatment of skin lesions is well detailed in the technical literature, as is the irritation caused by benzoyl peroxide. The effectiveness of benzoyl peroxide and typical problems associated with its use, such as excessive drying, heavy scaling, edema, burning, peeling, redness, excessive erythema, allergic contact dermatitis, and sensitization reactions, are discussed in the following references: Brogden, et al., Drugs, 8, 417 (1974); Poole, et al., Arch Derm. 102, 400 (1972); Eaglstein, arch. Derm. 97, 527 (1968); Pace, Can. Med. Ass. J. 93, 252 (1965); Vasarinsh, Arch. Derm. 98, 183 (1968); Myslibroski, et al., AFP 15, 86, (1977); Hare, Br. J. Clin. Prac. 29, 63 (1975); Fulton, et al., Arch. Derm. 110, 83 (1974); and Wilkinson, et al., Can. Med. Ass. J. 95, 28 (1966).

A reduction in, or control of, benzoyl peroxide irritation has been achieved by using certain gel formulations, or by temporarily suspending the topical application of the benzoyl peroxide compositions: Kuflik, et al., Cutis 17, 175 (1976); Liddell, Br. J. Clin. Prac. 28, 379 (1974); and Kirton, Br. J. Clin. Prac. 21, 127 (1967).

The guanidine compounds used herein are well known; Condensed Chemical Dictionary, Van Nostrand Reinhold Co., 7th Ed., page 461 and The Extra Pharmacopeia, Martindale, 24th Ed., Vol. 1, page 1372. Various uses of inorganic guanidine salts are also known. For example, U.S. Pat. No. 2,620,301, McLeod, Dec. 9, 1950, discloses the use of guanidine hydrochloride, carbonate, sulfate, and acetate in lubricant greases.

Guanidine compounds are also known for use as antimicrobial agents and fungicides. French Pat. 1,218,170, Scanley, Dec. 14, 1959, discloses the use of alkyl guanidines and their salts as bactericides and fungicides in cutting oils. U.S. Pat. No. 3,312,589, Entley, et al., Apr. 4, 1967, discloses the use of n-dodecylguanidine acetate in a formulation as a fungicide; U.S. Pat. No. 3,628,941, Marks, Dec. 21, 1971, discloses the use of n-dodecylguanidine hydrochloride as an antimicrobial agent in cutting oils; U.S. Pat. No. 3,152,181, Shapiro, et al., Oct. 6, 1964, discloses the use of monobiguanide compounds as antimicrobial agents. U.S. Pat. No. 3,769,427, Hughes, et al., Oct. 30, 1973, discloses the use of aromatic guanidine compounds and their salts as vasoconstrictors.

Attention is also drawn to the copending application of VanDuzee entitled "Skin Conditioning Compositions Containing Guanidine Inorganic Salts", Ser. No. 624,202, filed Oct. 20, 1975, which discloses the use of inorganic guanidine salts in cosmetic vehicles for moisturizing and conditioning skin and improving its flexibility.

None of the foregoing references suggests the use of guanidine compounds with peroxides in the manner of the present invention.

SUMMARY OF THE INVENTION

The present invention encompasses compositions of matter comprising mixtures of guanidine compounds and peroxide compounds, especially in cosmetic vehicles, for the treatment of skin lesions. It has been discovered that guanidine compounds ameliorate the skin irritation effects of peroxide compounds.

The use of peroxide compounds, especially benzoyl peroxide, for the treatment of acne and other skin lesions is well known. The use of guanidine compounds as fungicides and bactericides is also well known. The improvement provided by the present invention involves the conjoint use of these two types of compounds in the treatment of acne so that the peroxide can exert its healing effect while the guanidine compound exerts an assuasive effect so that the skin irritation often produced after prolonged topical use of the peroxide is reduced.

The present invention also encompasses an improved method for treating skin lesions, especially acne lesions, by topically applying a safe and effective amount of peroxide compound to the afflicted situs in conjunction with a guanidine compound, whereby skin irritation caused by the peroxide compound is reduced.

DETAILED DESCRIPTION OF THE INVENTION

The dermatological compositions herein comprise mixtures of toxicologically-acceptable peroxide compounds and toxicologically-acceptable guanidine compounds. These compositions are useful for the treatment of skin lesions, especially those of acne, with less skin irritation than normally occurs when only the peroxide compounds are used.

The compositions herein comprise a safe and effective amount of a guanidine compound and a safe and effective amount of a peroxide compound, all as described more fully hereinafter. Said guanidine and peroxide compounds can be used as solutions or as suspensions in the form of small (preferably impalpable) particles, said particles being suspended in insoluble form in a compatible fluid carrier, especially water or a pharmaceutically and cosmetically acceptable carrier.

By "safe and effective amount of a guanidine compound" herein is meant a sufficient amount of said guanidine compound to reduce skin inflammation, irritation, peeling, flaking, and other adverse effects resulting from the use of peroxide compounds, especially benzoyl peroxide. The amount of guanidine compound used will vary with the particular condition being treated, the severity of the condition, the duration of the treatment, the specific peroxide compound employed and its usage concentration, the severity of the reaction to the peroxide compound, and like factors within the specific knowledge and expertise of the patient or the attending physician.

By "safe and effective amount of a peroxide compound" herein is meant a sufficient amount of said peroxide compound to alleviate skin lesions at a reasonable benefit/risk ratio attendant with any medical treatment. Within the scope of sound medical judgment, the amount of peroxide compound used will vary with the particular condition being treated, the severity of the condition, the duration of the treatment, the specific peroxide compound employed and its concentration, and like factors within the specific knowledge and expertise of the patient or the attending physician.

By "toxicologically- or pharmaceutically-acceptable" herein is meant ingredients which are suitable for use in contact with the tissues of humans and lower animals without undue toxicity, irritation, allergic response, and the like, commensurate with a reasonable benefit/risk ratio.

By the term "comprising" herein is meant that various other, compatible drugs and medicaments, as well as inert ingredients and cosmetic vehicles, can be conjointly employed in the compositions and processes of this invention, as long as the critical guanidine compounds and peroxide compounds are used in the manner disclosed. The term "comprising" thus encompasses and includes the more restrictive terms "consisting of" and "consisting essentially of" which characterize the use of the essential ingredients in the manner disclosed herein.

By "applying topically" herein is meant directly laying on or spreading on epidermal tissue, especially outer skin.

By "afflicted situs" herein is meant a localized area of inflammation or lesion, and the immediate surrounding area.

By "skin lesion" herein is meant macules, patches, papules, plaques, nodules, comedones, burns, varicose and other skin ulcers, seborrhea, sycosis vulgaris, pustules, cysts, and similar afflictions treated medically by the application of peroxide compounds.

By "acne" herein is meant common acne, acne vulgaris, in all forms including papular, pustular, or cystic.

By "in conjunction with" herein is meant application of the guanidine compound either before, after, or at the same time as the application of the peroxide compound.

By "treating" herein is meant the topical use of the compositions herein on an afflicted situs and the process of topically applying a guanidine compound in conjunction with a peroxide compound to an afflicted situs.

By "particulate" herein is meant particles of the guanidine or peroxide compound within a size range below a diameter of about 0.1 mm. Particles below a diameter of about 0.05 mm are said to be "impalpable", inasmuch as they cannot be felt and recognized as particles on the skin of the average user and are preferred for use herein.

The guanidine compounds and peroxide compounds critical to the practice of this invention are disclosed more fully hereinafter. Other ingredients which can be included in the compositions to provide aesthetic and cosmetic benefits and to facilitate use are also disclosed hereinafter.

All percentages herein are by weight, unless otherwise specified.

The guanidine compounds (a term which includes the biguanides) used herein are of the formula:

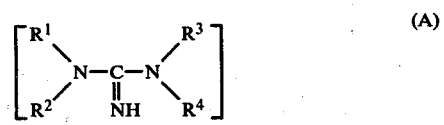
(A)

and organic or inorganic salts thereof; and the biguanides.

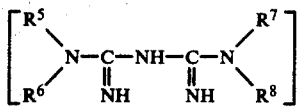

and organic or inorganic salts thereof, wherein each R group can be, for example, hydrogen, halogen, or organic substituents. Guanidine compounds comprise from about 1% to about 25% of the present compositions, preferably from 1% to 15%, and most preferably from 5% to 10%.

By "inorganic guanidine compounds" herein is meant compounds of the above formulae wherein the R groups are hydrogen. Salts formed by reacting inorganic or organic acids and inorganic guanidine free bases are common inorganic guanidine compounds. Preferred inorganic guanidine compounds are inorganic guanidine salts such as guanidine hydrobromide, guanidine sulfate, guanidine bisulfite, guanidine carbonate, guanidine phosphate, and most preferably, guanidine hydrochloride.

Organic guanidine compounds as used herein include guanidine compounds wherein any one or more of the R groups in the above formulae are organic substituents. Organic guanidine compounds may also be converted into salts by reacting the selected organic guanidine free base with an appropriate inorganic or organic acid. Preferred acids include hydrochloric, sulfuric, nitric, hydrobromic, hydroiodic, maleic, citric, acetic, tartaric, benzoic, propionic, and carbonic acids, all of which are well known for their formation of pharmaceutically acceptable salts.

Alkyl guanidine compounds as used herein include guanidine compounds wherein $R^1$, $R^2$, $R^3$, or $R^4$ are alkyl groups having from one to eighteen carbon atoms, preferably from one to ten carbon atoms and most preferably are methyl guanidine, ethyl guanidine or n-dodecyl guanidine. Alkyl guanidines are typically produced by the reaction of a substituted or unsubstituted cyanamide with a primary or secondary amine hydrochloride, for example, cyanamide with methylamine hydrochloride to produce methyl guanidine hydrochloride.

Aromatic guanidine compounds as used herein include compounds of formula (A) wherein one or more R groups are aryl substituents. Aromatic guanidine compounds are known compounds which are typically produced by the reaction of a substituted or unsubstituted cyanamide with an aryl amine hydrochloride, for example, cyanamide with aniline hydrochloride to produce phenyl guanidine hydrochloride.

Biguanide compounds used herein include monobiguanide compounds of formula (B) wherein the R groups are hydrogen or organic substituents such as $C_1$-$C_{20}$ alkyl, alkenyl, alkaryl, alkoxyalkyl, cycloalkyl, aralkyl, haloaralkyl, aryl, and haloaryl.

Typical biguanide compounds are prepared by the aminolysis of bicyanodiamides, for example, dicyanoamide with methylamine hydrochloride to form methyl biguanide hydrochloride. Further details of the preparation of the guanidine compounds are found in the texts, OPEN CHAIN NITROGEN COMPOUNDS, Vol. I, Benjamin, 1965, and THE CHEMISTRY OF ORGANIC CYANOGEN COMPOUNDS, Reinhold, 1947.

Other especially useful guanides are those disclosed in U.S. Pat. Nos. 3,152,181 and 3,769,427 incorporated herein by reference.

The term "peroxide compounds" as used herein encompasses compounds of the formula $R_1$—O—O—$R_2$, where $R_1$ and $R_2$ are hydrogen or organic substituents. Preferred peroxide compounds include hydrogen peroxide and its salts and substituted or unsubstituted benzoyl peroxide, the most preferred compound being benzoyl peroxide. All such peroxides are items of commerce. Peroxide compounds comprise from about 1% to about 25% of the compositions, preferably from 1% to 15% and most preferably from 5% to 10%.

In addition to the guanidine compounds and peroxide compounds, the compositions described herein can include any cosmetic vehicle which does not react with the guanidine compound or the peroxide compound. Typical compositions may include emollients such as hydrocarbon oils and waxes, lanolin and lanolin derivatives, silicone oils, triglyceride esters, fatty acids, fatty alcohols, alkyl and alkenyl esters of fatty acids, polyhydric alcohols and polyether derivatives, wax esters, and beeswax derivatives. Such emollients preferably comprise from 10% to 50% of the compositions.

Emulsifiers of the nonionic, anionic, or cationic classes can also be used, and will usually comprise from 1% to 10% of the composition. Suitable emulsifiers include nonionic emulsifiers, such as fatty acid monoglycerides, fatty alcohols, polyethylene glycols, and propylene glycols, anionic emulsifiers, such as alkyl ethoxy ether sulfonates, ammonium alkyl sulfates, and fatty acid soaps, and cationic emulsifiers, such as quaternary ammonium, morpholinium and pyridinium compounds. When an emollient which has emulsifier properties is used, less additional emulsifier is necessary.

Chelating agents such as EDTA, nitrilotriacetate, and gluconic, citric, and tartaric acids, preferably at a level of from 0.01% to 1% of the composition, are used to avoid the decomposition of the peroxide compound by metal ions.

Optional components such as finely divided sulfur, USP grade, at a level of from 1% to 25% of the composition, thickening agents, such as methyl cellulose, cross-linked carboxyl polymethylene polymers, bentonite, gum tragacanth, gum kharaya, and polyethylene glycols, at a level of from 1% to 10% of the composition, and trace amounts of fragrance materials such as perfumes can also be used. The balance of the composition comprises water.

The compositions are typically prepared by thoroughly blending all of the components together in admixture and milling, if necessary, to reduce all particles to impalpable size. The benzoyl peroxide should be of high purity, on the order of 97% to 100% pure, and in the form of a finely divided powder. The powder may be either wet or dry, but is preferably wet for ease of handling and safety. If wet benzoyl peroxide is used, it may be necessary to grind the crystals before admixture or to mill the composition after admixture and blending to reduce the crystals to impalpable size. Preferably, the milling or grinding operation is performed in the cold to prevent decomposition of the peroxide by localized friction.

The following examples illustrate the present methods and compositions, but are not intended to be limitations thereof. The compositions are typically applied twice daily to acne lesions. The typical usage rate is about 0.001 g/cm$^2$ skin to about 0.5 g/cm$^2$ skin, per application, but this can vary with the user, the severity of the affliction, and the concentrations of guanidine compound and peroxide compound in the particular composition being used.

EXAMPLE I

| ANTI-IRRITANT COMPOSITION A | |
|---|---|
| Guanidine.HCl | 5% |
| Propylene glycol | 14% |
| PEG 400 | 6% |
| Water | Balance |

| TREATMENT COMPOSITION B | |
|---|---|
| Benzoyl peroxide | 5% |
| Gum tragacanth | 10% |
| Water | Balance |

Admix and thoroughly blend Compositions (A) and (B). Mill Composition (B) until all particles are impalpable. Apply Composition (B) to acne lesions at a rate of about 0.01 g/cm² skin twice per day. Either immediately after or immediately before each application of (B), apply (A) at the same rate.

Acne lesions treated in the foregoing manner over a two-week period are markedly improved with reduced incidence of irritation by the benzoyl peroxide.

EXAMPLE II

| Ethyl guanidine | 10% |
|---|---|
| Benzoyl peroxide | 10% |
| Poloxyethylene lauryl ether | 6% |
| Acidified colloidal magnesium aluminum silicate gel and water | Balance |

Admix and carefully and thoroughly blend the component. As necessary, carefully mill the composition until all particles are impalpable. Apply 0.05 g/cm² skin twice a day to the acne lesions.

EXAMPLE III

| N¹ - (lauroxypropyl) biguanide | 15% |
|---|---|
| Benzoyl peroxide | 5% |
| Ethyl stearate | 17% |
| Sorbitol | 15% |
| Water | Balance |

Admix and carefully and thoroughly blend the components. As necessary, carefully mill the composition until all particles are impalpable. Apply twice daily at 0.5 g/cm² skin twice a day to the acne lesions.

EXAMPLE IV

| Phenyl guanidine hydrochloride | 5% |
|---|---|
| Benzoyl peroxide | 5% |
| Methoxypolyethylene glycol | 10% |
| Diethylene glycol | 5% |
| Bentonite | 5% |
| Water | Balance |

Admix and blend the components. As necessary, mill carefully until all particles are impalpable. Apply topically to acne lesions twice a day at 0.01 g/cm² skin.

EXAMPLE V

| Methyl guanidine carbonate | 5% |
|---|---|
| Hydrogen peroxide | 5% |
| EDTA | 0.5% |
| Sulfur (colloidal) | 2% |
| Stearic acid | 10% |
| Water | Balance |

Admix and blend the components. Apply topically to acne lesions twice a day at 0.05 g/cm² skin.

The compositions of Examples IV and V may also be used topically in the treatment of seborrhea at the same rate of application.

Further examples include the composition of Example IV wherein the phenyl guanidine hydrochloride is replaced by alkoxypropyl biguanides as disclosed in U.S. Pat. No. 3,152,181, for example, N¹-(lauroxypropyl), N⁵-(dibenzyl)-biguanide; N¹-(lauroxypropyl)-N⁵-(methyl),N⁵-(2,4-dichlorobenzyl)-biguanide; and N¹-(lauroxypropyl),N⁵-(2,4-dichlorobenzyl)-biguanide. The phenyl guanidine hydrochloride of Example IV may also be replaced by aromatic guanidine compounds as disclosed in U.S. Pat. No. 3,769,427, for example, 3'-chloro-4'-hydroxyphenylguanidine hydrochloride and 3'-fluoro-4'-tolyguanidine nitrate. Still further examples include the composition of Example IV wherein the phenyl guanidine hydrochloride is replaced by N¹-dimethyl guanidine citrate; n-dodecyl guanidine carbonate; N¹-dibutylguanidine; N¹-amoxyguanidine hydrochloride; N¹-(1-hydroxyethyl) guanidine tartrate; and N¹-dimethoxy guanidine.

As can be seen from the foregoing, compositions of the present invention comprising a guanidine material and a peroxide, conveniently at a weight ratio in the range of about 10:1 to 1:10 and preferably about 1:1 to about 2:1, provide excellent therapy for acne and like diseases.

What is claimed is:

1. A dermatological composition for treating skin lesions comprising a keratolytically effective amount of benzoyl peroxide and an amount for reducing the skin irritation thereof of a compound selected from the group consisting of guanidine hydrochloride, guanidine sulfate, guanidine carbonate, and guanidine phosphate.

2. A process of treating skin lesions comprising topically applying the composition of claim 1 to the afflicted situs.

* * * * *